(12) United States Patent
Benditte-Klepetko (10) Patent No.: US 11,227,424 B2
(45) Date of Patent: *Jan. 18, 2022

(54) METHOD AND SYSTEM TO PROVIDE A COMPUTER-MODIFIED VISUALIZATION OF THE DESIRED FACE OF A PERSON

(71) Applicant: QuantiFace GmbH, Vienna (AT)

(72) Inventor: Heike Benditte-Klepetko, Vienna (AT)

(73) Assignee: QUANTIFACE GMBH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 17/331,121

(22) Filed: May 26, 2021

(65) Prior Publication Data

US 2021/0279933 A1    Sep. 9, 2021

Related U.S. Application Data

(63) Continuation of application No. 17/117,805, filed on Dec. 10, 2020.

(30) Foreign Application Priority Data

Dec. 11, 2019 (EP) .................................. 19215134

(51) Int. Cl.
*G06K 9/00* (2006.01)
*G06K 9/62* (2006.01)
(Continued)

(52) U.S. Cl.
CPC .......... *G06T 11/60* (2013.01); *G06K 9/00281* (2013.01); *G06K 9/6256* (2013.01);
(Continued)

(58) Field of Classification Search
CPC .......... G06T 7/00; G06T 7/0012; G06T 11/00; G06T 11/60; G06T 15/00; G06T 19/00;
(Continued)

(56) References Cited

U.S. PATENT DOCUMENTS 9,875,391 B2    1/2018    Liang et al.
10,289,897 B2   5/2019    Tang et al.
(Continued)

FOREIGN PATENT DOCUMENTS

WO    2015/017687 A2    2/2015

OTHER PUBLICATIONS

Qin, R., et al., "Modem Physiognomy: An Investigation on Predicting Personality Traits and Intelligence from Human Face", Arxiv.org, Cornell University Library, Ithaca, NY (Apr. 26, 2016).
(Continued)

*Primary Examiner* — Matthew Salvucci
(74) *Attorney, Agent, or Firm* — Merchant & Gould P.C.

(57) ABSTRACT

A data set of visuals of faces and extracted face property data are generated and linked to face characteristics data provided by a representative set of humans that rate the visuals of these faces with respect to their face characteristics. Further face property data of these visuals of faces is extracted and together with the generated data set used to train an artificial intelligence. The artificial intelligence is used to analyse a visual of the person's face and generate a data set of modifications based on a selected desired characteristic(s) and modifications achievable by at least one cosmetic and/or medical treatment. The visual of the face of the person is modified based on the data set of modifications and the computer-modified visual of the desired face of the person with the modification of the face achievable by the least one proposed cosmetic and/or medical treatment is generated and displayed.

24 Claims, 7 Drawing Sheets

(51) Int. Cl.
*G06N 5/00* (2006.01)
*G06N 7/00* (2006.01)
*G06N 20/00* (2019.01)
*G06T 11/60* (2006.01)
*G06T 7/00* (2017.01)

(52) U.S. Cl.
CPC .............. *G06N 5/00* (2013.01); *G06N 7/00* (2013.01); *G06N 20/00* (2019.01); *G06T 7/0012* (2013.01); *G06T 2200/24* (2013.01); *G06T 2207/10148* (2013.01); *G06T 2207/20081* (2013.01); *G06T 2207/30201* (2013.01)

(58) Field of Classification Search
CPC ....... G06T 2200/24; G06T 2207/10148; G06T 2207/20081; G06T 2207/30201; G06K 9/00281; G06K 9/6256; G06N 5/00; G06N 7/00; G06N 20/00
USPC .......................................................... 345/633
See application file for complete search history.

(56) References Cited

U.S. PATENT DOCUMENTS

| | | | |
|---|---|---|---|
| 10,387,714 B2 | 8/2019 | Han et al. | |
| 10,482,333 B1 | 11/2019 | el Kaliouby et al. | |
| 10,764,535 B1 | 9/2020 | Powell et al. | |
| 10,796,480 B2 | 10/2020 | Chen et al. | |
| 10,825,564 B1* | 11/2020 | Zhang | A61B 5/7267 |
| 10,997,703 B1* | 5/2021 | Khalatian | G06T 7/0002 |
| 11,151,362 B2 | 10/2021 | Velthuis et al. | |
| 2012/0257800 A1 | 10/2012 | Zheng | |
| 2013/0069940 A1 | 3/2013 | Sun et al. | |
| 2016/0307027 A1 | 10/2016 | Liang et al. | |
| 2018/0293802 A1 | 10/2018 | Hendricks et al. | |
| 2018/0315063 A1 | 11/2018 | Cheesman | |
| 2018/0342110 A1 | 11/2018 | Miao | |
| 2019/0005306 A1* | 1/2019 | Wu | G06K 9/00255 |
| 2019/0005359 A1 | 1/2019 | Wilf et al. | |
| 2021/0012097 A1* | 1/2021 | Velthuis | G06K 9/00288 |
| 2021/0089759 A1 | 3/2021 | Todorov et al. | |

OTHER PUBLICATIONS

Kamenskaya, E., et al., "Recognition of Psychological Characteristics from Face", Metody Informatyki Stosowanej, Gdansk Poland, http://www.uniphiz.com/digital_physiognomy/recognition-of-pyschological-characteristics-from-face.pdf (2008).

Jacques, Jr., J.C.S., et al., "First Impressions: A Survey on Vision-Based Apparent Personality Trait Analysis", Arxiv.org, Cornell University Library, Ithaca, NY (Apr. 22, 2018).

Messer, U., et al., "Predicting Social Perception from Faces—A Deep Learning Approach", Arxiv.org, Cornell University Library, Ithaca, NY, (Jun. 29, 2019).

Liao, Y., et al., "Deep Rank Learning for Facial Attractiveness", 2017 4th IAPR Asian Conference on Pattern Recognition (ACPR), IEEE, (Nov. 26, 2017).

European Search Report, Application No. EP 19 21 5134, dated Jul. 17, 2020.

European Search Report, Application No. EP 19 21 5139, dated Jun. 16, 2020.

Klepetko, H., "Facial Characteristics and First Impression: wie der 'Erste Eindruck' die Wahl der Therapie beeinflussen kann," Schein & Sein, Austria, Sep. 12-14, 2019.

Klepetko, H., "Facial Characteristics: Letting Social Judgment Determine our Choice of Treatment," International Society of Plastic Surgery (ISAPS), 2018.

* cited by examiner

DOMINANT

COMPETENT

Fig. 11

| Dominant | | | | | | | | | |
|---|---|---|---|---|---|---|---|---|---|
| Face Area | zygoma | lower eyelid | lips | chin | cheek | jawline | eyebrows | marionett line | glabella |
| Action | more volume | | | | more volume | more volume | lower | | |
| Treatment | fillers | | | | fillers | fillers | botox | | |
|  | facelift | | | | facelift | | | | |
| Competent | | | | | | | | | |
| Face Area | zygoma | lower eyelid | lips | chin | cheek | jawline | eyebrows | marionett line | glabella |
| Action | | | | less wide | less full | | lower | | |
| Treatment | | | | bone correction | fat reaction | | botox | | |
|  | | | | facelift | lipolysis | | | | |
|  | | | | filler | filler | | | | |
| Trustworthy | | | | | | | | | |
| Face Area | zygoma | lower eyelid | lips | chin | cheek | jawline | eyebrows | marionett line | glabella |
| Action | | | higher lateral | less wide | pronounced cheekbones | | higher medial | | |
| Treatment | | | fillers | bone correction | fillers | | botox | | |
|  | | | botox | facelift | | | | | |
|  | | | surgical correction | filler | | | | | |
| Younger | | | | | | | | | |
| Face Area | zygoma | lower eyelid | lips | chin | cheek | jawline | eyebrows | marionett line | glabella |
| Action | more volume | smooth | fuller | | | straight | lateral | smooth | smooth |
| Treatment | fillers | blepharoplasty | fillers | | | facelift | botox | fillers | botox |
|  | facelift | fillers | surgical correction | | | fillers | fillers | botox | fillers |
|  | | botox | | | | threats | threats | threats | threats |
|  | | | | | | | eyebrow lift surgical | facelift | |

METHOD AND SYSTEM TO PROVIDE A COMPUTER-MODIFIED VISUALIZATION OF THE DESIRED FACE OF A PERSON

CROSS REFERENCE TO RELATED APPLICATION

This application is a continuation of U.S. patent application Ser. No. 17/117,805, filed Dec. 10, 2020, which claims benefit of European Patent Application Serial No. 19215134.8, filed Dec. 11, 2019, and which applications are incorporated herein by reference in their entirety. To the extent appropriate, a claim of priority is made to the above disclosed applications.

BACKGROUND

The present invention relates to a method and system to provide a computer-modified visualization of a desired face of a person who considers undergoing a minimally invasive and/or invasive cosmetic and/or medical treatment to improve the person's appearance. There is a general wish to optimize the own appearance. The face is one of the main areas of the body relevant for this appearance. There are many different treatments known to change the facial appearance, expression and/or morphology, e.g. reduction of wrinkles in the skin of the face or modification of the cheekbones. A person interested in such a change typically makes an appointment with a beautician, dermatologist, physician, specialist certified to do facial modifications, or plastic surgeon to get information about possible treatments. In a first step the specialist mentioned above inspects the different regions of the face and based on their personal knowledge and skills proposes medical and/or cosmetic treatments that could provide the desired change of the appearance. The problem of this way of working is that it is difficult for the person to understand the possible visual effects and/or effects on the first impression (i.e., how the face is perceived by others) of the treatments the specialist proposes.

LIAO YANBING ET AL: "Deep Rank Learning for Facial Attractiveness", 2017 $4^{TH}$ IAPR ASIAN CONFERENCE ON PATTERN RECOGNITION (ACPR), IEEE, 26 Nov. 2017 (2017-11-26), pages 565-570, XP033475316 discloses a Deep Convolutional Neuronal Network and artificial intelligence for fully automatic facial beauty assessment and ranking. A "HOTorNOT" database of 1.885 female face images collected from a popular social/dating website was used to train the artificial intelligence how to predict facial attractiveness of female faces and rank them.

MESSER U ET AL: "Predicting Social Perception from Faces: A Deep Learning Approach", ARXIV.ORG, CORNELL UNIVERSITY LIBRARY, 201 OLIN LIBRARY CORNELL UNIVERSITY ITHACA, N.Y. 14853, 29 Jun. 2019 (2019-06-29), XP081385771 discloses a Deep Convolutional Neuronal Network and artificial intelligence to predict human perceiver's impression of the characteristics "warmth" and "competence" based on a visual representation of a face of a person. The artificial intelligence extracts features or face property data from regions of face images and was trained with a 10K Adults Face database where human raters rated the characteristics "warmth" and "competence" of these faces to generate face characteristics. Heat maps were used to identify regions of faces relevant for human perceivers.

WO 2015/017687A2 discloses a method and system that enables a user to take a picture of their face with a device and send it to a computer server. The server uses a facial recognition software to identify anatomical features of the face and the user selects the anatomical area of his face he wants to improve. In a next step, the server determines the level of "severity" of a defect in the selected anatomical area. After that, the person has to select a medical or cosmetic treatment from a list of possible treatments and the server determines the likely treatment outcome based on data of clinical studies for this selected medical or cosmetic treatment. Finally, the server generates a modified picture of the user's face with the likely outcome of the selected medical or cosmetic treatment for the selected anatomical area, which picture is displayed at the user's device next to the original picture taken. The disclosed method provides the disadvantage that a user is left alone both with the selection of facial regions and with the selection of possible medical or cosmetic treatments which might lead to an overall less attractive appearance of the user after one or more treatments. There is a need for technical means to solve these technical selection problems.

SUMMARY

These problems are solved with a method that comprises the following steps:
Generate a data set of visuals of faces and extracted face property data thereof linked to face characteristics data provided by a representative set of humans that rate the visuals of these faces about their face characteristics and store the data set in a database;
Extract further face property data of these visuals of faces and use these extracted face property data together with the generated data set for training of an artificial intelligence to enable the artificial intelligence to provide an automated rating of the characteristics of the visuals of faces;
Generate a data set of visual modifications of a face achievable by cosmetic and/or medical treatments and store the data set in a database;
Take a standardized visual of the face of the person;
Input at least one desired characteristic of the face of the person to be changed;
Use the artificial intelligence to analyse the visual of the person's face and to generate a data set of modifications based on the selected desired characteristic(s) and modifications achievable by at least one cosmetic and/or medical treatment;
Modify the visual of the face of the person based on the data set of modifications and generate the computer-modified visual of the desired face of the person with the modification of the face achievable by at least one cosmetic and/or medical treatment;
Display the computer-modified visual of the desired face of the person.

This inventive method, system and/or computer program uses a complete different concept and technique to enable an informed decision for a user how to change the facial appearance, expression and/or morphology. The user may be for example, a beautician, dermatologist, physician, specialist certified to do facial modifications or plastic surgeon, as well as a person interested in a change of their own appearance.

The invention is based on the finding that when aiming to change a person's appearance it is only a secondary goal to e.g. selectively reduce frown lines or to increase the volume of the lips, since persons categorize the appearance of others in the course of forming a first impression in a more complex way and as a whole. Characteristics attributed to a person when making a first impression are, for example, attractiveness, healthiness, youthfulness, tiredness, sadness, friendliness, dominance, competence, likability or trustworthiness just to name some of these. The new concept and technique enables a user to select at least one characteristic she/he wants to change. A change in a characteristic attributed by others during forming the first impression can be achieved in both ways, i.e. increasing a characteristic which is perceived as positive or decreasing a characteristic which is perceived as negative. For example, a person might wish to appear less tired. In another example, a person might wish to appear more friendly. In a further example, a person might wish to appear more attractive.

In a first step of the inventive method, a new data set of visuals of faces is compiled. This includes images and videos of people's faces as well as computer-generated images and 3D models of artificial faces. In a pre-processing step for the deep learning algorithm, this data set is normalized via transformations for face alignment, cropping and resizing. Facial landmark detection of face properties first and then more detailed like skin texture analysis are performed in order to properly align face data. The data set of visuals is generated and improved with human assessments and/or modifications of such faces to train a deep learning based application and/or artificial intelligence and/or software. The quality of this application is further refined in an iterative process using data generated by previous versions of itself. Reference is made to above cited scientific articles as state of the art documents that describe the structure and model architecture of such an artificial intelligence.

According to deep learning principles, a new technique is used to generate a data set of modifications that comprise complex information about all modifications of the face needed to change the user's characteristics in the desired direction. The modifications might affect the facial appearance, expression and/or morphology. Such modifications of the face may comprise, for example, height of the eyebrows, fullness of the cheeks, width and height of the chin, volume of the lips, volume of the zygoma, depth of the marionette lines, straightness of the jaw line, depth of the glabellar lines, periorbital hollowness and skin tightness. Technically, these changes can be obtained by minimally invasive and/or invasive cosmetic and/or medical treatments, as has been proven by clinical studies or treatments performed in the past. These treatments include application of dermal fillers, Botulinum toxin, threads, implants, surgery, laser treatments, autologous fat transplantation, and skin resurfacing treatments amongst others.

In a further step, visual data of the face of the person (e.g. photos or videos) are obtained. Together with a selection of at least one characteristic to be changed, the data set of visuals of faces are transferred to a server. The additional input of age and/or gender and/or ethnicity data of the person is possible as well.

In a final step of the method, a deep learning based application/artificial intelligence processed by the server is used to modify the visual data of the user's face according to the user's selected change of one or more characteristics. The artificial intelligence can also be used to optionally describe and/or rate the characteristics based on the original visual data of the person's face.

The computer-modified visualization of the desired face can be shown on a display next to the original visual data of the user to show the possible change. This change may be obtained by using one or a combination of different invasive and/or minimally invasive cosmetic and/or medical treatments that in sum modify the user's face towards the desired change of the selected characteristic(s). Optionally, a proposal for the necessary treatments to achieve the desired face can be given.

This new method provides the major advantage that it visualizes the effect of changes of the facial appearance, expression and/or morphology on the characteristics attributed to a person when making a first impression. The user has the option to choose at least one specific characteristic he/she wishes to change (e.g. reduce or improve). Subsequently, the needed changes of the facial appearance, expression and/or morphology, which are necessary to reach the desired effect (i.e. the desired face), are visualized.

Methods according to the state of the art visualize only changes of isolated regions of the face. In the context of characteristics attributed to a person when making a first impression the face of the user might be changed in a not desired way. The main aim of a businessman or politician might be to improve his appearance towards being perceived as a competent person while at the same time he wishes to appear younger. However, the selected changes in the facial characteristics to look younger might result in a less competent appearance contradicting his professional needs.

The inventors found that taking into consideration one or more characteristics attributed to a person when making a first impression is essential for optimizing the choice and/or selection of individualized different invasive and/or minimally invasive cosmetic and/or medical treatments in order to reach the desired modification of the face. One of the requirements for applying this principle is the ability to process large data sets in a novel, innovative, fast and efficient way via using an artificial intelligence.

Therefore, the invention solves the technical problem of prior art to process data in order to analyse, visualize and predict a person's face and its perception by others according to characteristics attributed to the person when making a first impression, by a combination of steps listed above.

BRIEF DESCRIPTION OF THE DRAWINGS

These and further advantageous embodiments of the invention will be explained based on the following description and the accompanying drawings.

DETAILED DESCRIPTION

Figure 1:
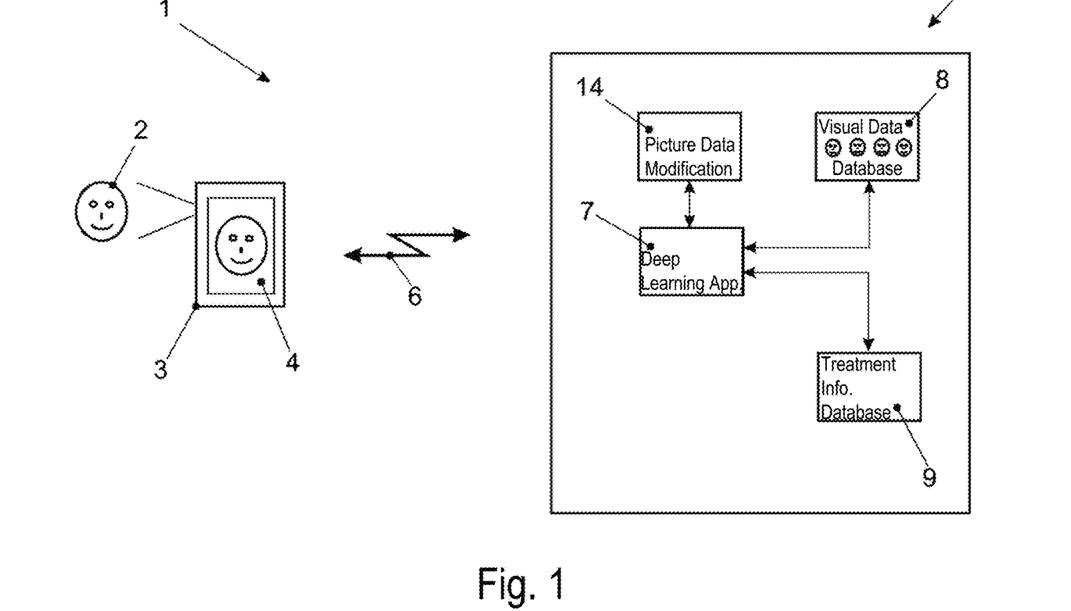
FIG. 1 shows a system to display a computer-modified visualization of a desired face of a person.
Figure 2:
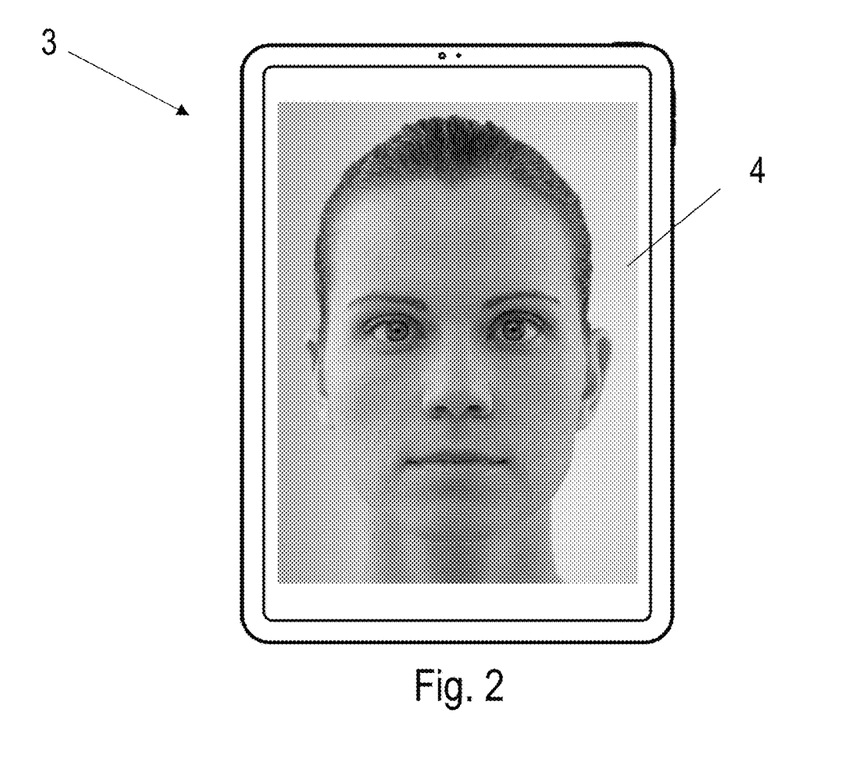
FIG. 2 shows a mobile device of the system with a picture of the face of the person.

FIG. 1 shows a system 1 to display a computer-modified visualization or visual of a desired face of a person 2 with a mobile device 3. The mobile device 3 processes a software and in particular an App for person 2, who considers undergoing an invasive and/or minimally invasive cosmetic and/or medical treatment, or for a specialist performing such treatment who would like to take a data-driven decision which treatments to choose to obtain the desired changes of the face. A camera of the mobile device 3 is used to obtain the visual of the face of person 2 as standardized visual data 4 shown in FIG. 2. Visual data 4 may represent a photo or a film of the face of person 2. Standardization of the visual data 4 may be split into instructions for person 2 and the photographer what to do for taking a standardized photo or film and into a post-processing of the photo or film taken. The instructions for person 2 and the photographer may include one or more of the following steps: ask person 2 to take off e.g. earrings or a nose ring; ask person 2 not to smile, ask person 2 to make a neutral facial expression; ask person 2 to keep head hair out of his/her face; ask person 2 to look straight into the camera; good general condition of lightning; neutral background. The post-processing of the photo or film may include one or more of the following steps: cut-out the background behind the face from the visual data 4; cut-out the ears of the person's face to reduce the visual influence of e.g. earrings; cut-out clothes and other wardrobe that might influence with the face; cut-out the head hair of the person 2.

System 1 comprises a remote server 5 connected via a broadband network 6 or other remote connection technology with the mobile device 3. The server 5 processes a deep learning based application 7 and as such forms an artificial intelligence that analyses visual data 4 of the face of person 2 to rate one or more characteristics attributed to a person 2 when making a first impression. Such face characteristics or traits may for example be attractiveness, healthiness, youthfulness, tiredness, sadness, friendliness, dominance, competence, likability or trustworthiness. The deep learning based applications 7 is a computer program comprising instructions which, when the program is executed by remote server 5, causes remote server 5 to carry out the following steps to provide a computer-modified visualization 13 of a desired face of person 2.

Figure 3:
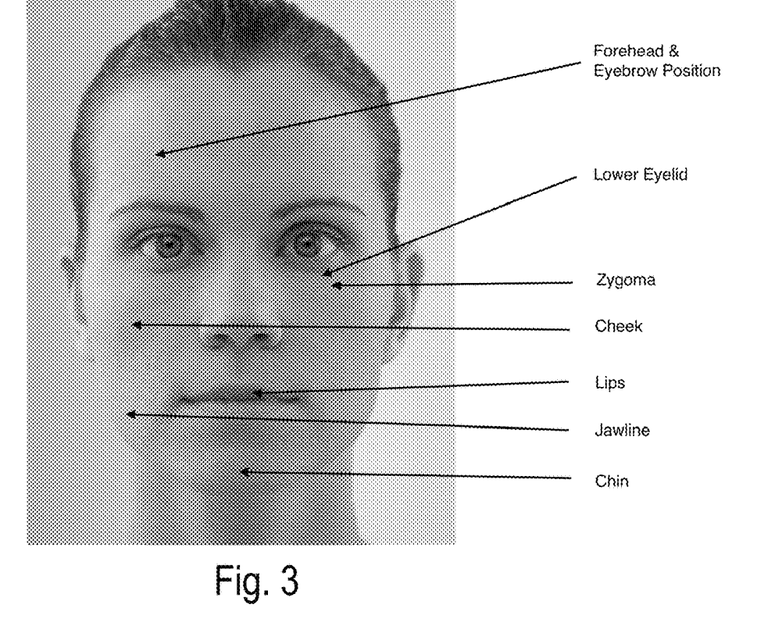
FIG. 3 shows in which regions the face of the person is divided for further analyses.

To enable the deep learning based application 7 to rate face characteristics the following steps are processed. In a first step a data set of visual data of visuals of faces and extracted face property data thereof linked to face characteristics data is generated. To extract face properties conventional computer vision algorithms like a landmark detection divide the face of person 2 in regions like the chin and the jawline as shown in FIG. 3 and automatically extracts characteristics and their location in the face. Such face property data may for instance include the distance between the eyes or the distance between the eyes and the mouth and other distances to be measure to describe a face. These face property data are stored together with the visual data of these faces by the deep learning based application 7 in a database 8 of the server 5. A representative number of such visuals of faces stored as visual data in database 8 are shown on a display to a representative number of humans to manually rate these visuals of faces about their characteristics. The humans may rate them with scores (e.g. from 0 to 7) for different characteristics or traits. These human ratings are stored in database 8 linked to the visual data of the faces and provide a basis information for the deep learning based application 7 to rate characteristics attributed to a person 2 when making a first impression.

Figure 4:
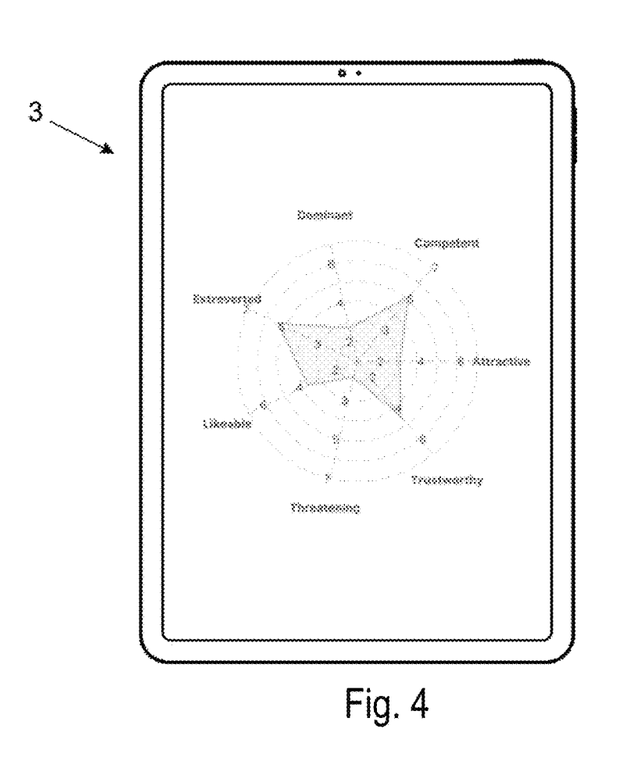
FIG. 4 shows a description and rating of the characteristics based on the original visual data of the person's face.

In a second step further face property data of these visuals of faces are extracted by conventional computer vision algorithms for example landmark detection, wrinkle detection, skin texture analysis, analysis of facial proportions. These face property data of visuals of faces are used together with the data set generated and stored in database 8 in the first step for training of the deep learning based application 7 to enable the artificial intelligence to provide an automated rating of the characteristics of the visuals of faces. Reference is made to the scientific articles listed above that describe the structure and model architecture of such an artificial intelligence. As a result, any visual of a face may be provided to the deep learning based application 7, which will, based on the data set stored in database 8, provide an automated rating of the characteristics of the visuals of the face. FIG. 4 shows the result of such a description and automated rating of the characteristics or traits of a person based on the visuals of the person's face displayed on mobile device 3.

Figure 12:
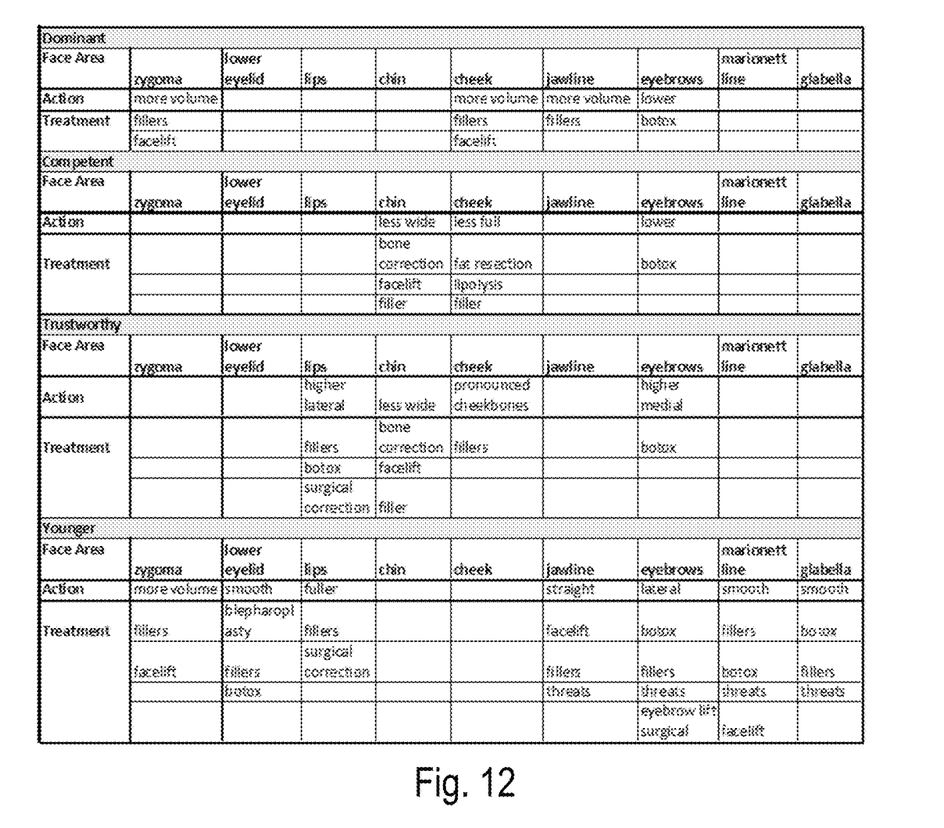
FIG. 12 shows a table with examples of invasive and/or minimally invasive cosmetic and medical treatments to achieve changes of desired characteristics of a person's face by actions in particular regions of the face of the person.

Server 5 furthermore comprises a database 9 with data generated in a third step based on clinical studies, case studies or other publicly available information, which data comprise information about visual modifications of a face achievable by invasive and/or minimally invasive cosmetic and medical treatments. This database 9 for instance comprises information of the effectiveness of a treatment improving a wrinkle score of 3.1 to 1.5 within 3 weeks. Reference is made to prior art WO 2015/017687 that discloses parameters-based clinical trial summaries, for example the investigator's rating of glabellar line severity at maximum frown and the subject's global assessment of change in appearance of glabellar lines after a medical treatment with Botox over a time period of 120 days post-injection. This prior art document discloses a database that stores data how to improve one particular area of a face with one particular medical treatment. FIG. 12 as one further example shows a table, which includes the information of database 9 with examples of invasive and/or minimally invasive cosmetic and medical treatments to achieve actions or improvements in particular regions of the face of person 2.

After databases 8 and 9 have been setup with above described three steps, system 1 is ready to be used to provide computer-modified visuals of a face of a person as described in the following steps of the method.

In a fourth step the camera of mobile device 3 is used to obtain the standardized visual data 4 of the face of person 2 as described above and shown in FIG. 2. In a preferred optional embodiment, these visual data 4 are sent to sever 5 and deep learning based application 7 processes an automated rating of the characteristics or traits of person 2 and provides the rating shown in FIG. 4 to support person 2 to decide which characteristic or trait he/she might want to change. In another less preferred embodiment person 2 makes his/her decision which characteristic of his/her face to improve without the automated rating shown in FIG. 4.

Figure 5:
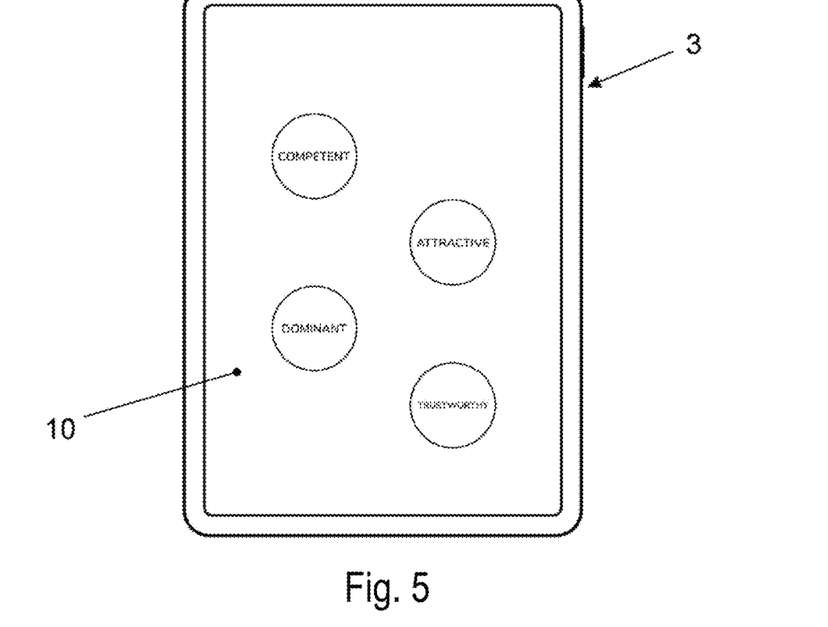
FIG. 5 shows how characteristics may be selected by the user.

In a fifth step person 2 inputs at least one characteristic of the face of the person to be changed based on the personal interest of person 2. The characteristic(s) input by person 2 is stored and transmitted in the form of face characteristics data. The person 2 may decide to change his/her facial appearance, expression and/or morphology for improving the characteristic "competent" with input means 10 of mobile device 3 as shown in FIG. 5. This characteristic selected by person 2 is transmitted via broadband network 6 to server 5. In another embodiment of the invention person 2 may use another way to input the at least one characteristic of the face he/she is interested to change with mobile phone 3. This may be done by the selection of the App used by person 2, as there may be an App to improve the characteristic "competent" and another App to improve the characteristic "dominant".

Figure 11:
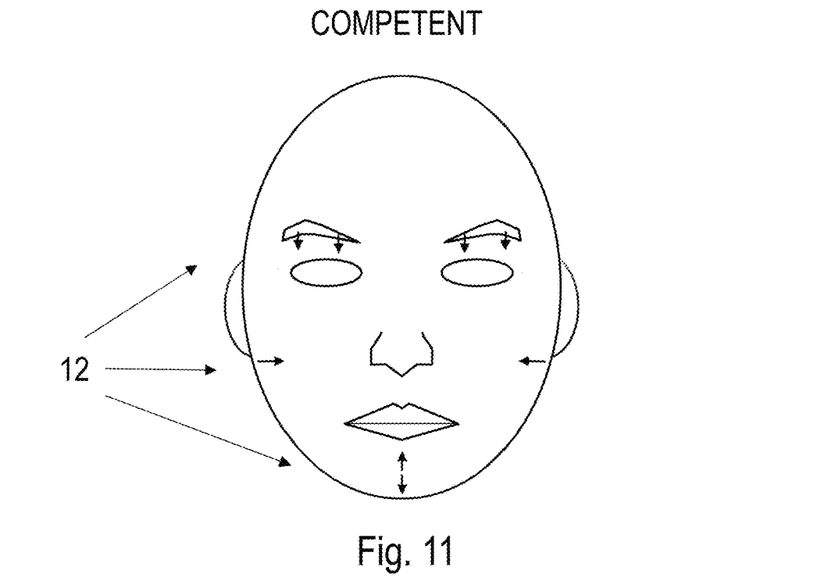
FIG. 11 shows a line drawing of a face with regions of the face marked to be treated to increase the characteristic "competence" attributed to a person when making a first impression.

In a sixth step of the method the artificial intelligence of the server 5 analyses the visual of the person's face and generates a data set of modifications 12 based on the selected desired characteristic(s) and modifications achievable by at least one cosmetic and/or medical treatment of database 9. This means that either only one or more cosmetic treatments or only one or more medical treatments or any combination of one or more cosmetic and medical treatments of database 9 may be used to modify the user's face towards the desired change of the selected desired characteristic(s). Furthermore, references to a cosmetic treatment are meant to cover any invasive and/or minimally invasive cosmetic treatment. To achieve this technical step, the deep learning based application 7, based on database 8, evaluates which modifications are needed to improve the characteristic "competent" of person 2 and matches these modifications needed with modifications possible as stored in database 9. FIG. 11 shows a line drawing of a face with regions of the face marked to be treated to increase the characteristic "competent" attributed to a person when making a first impression. In line with that, the table of FIG. 12 shows the actions needed to increase the characteristic "competent" attributed to person 2 when making a first impression: make the chin less wide and the cheeks less full and lower the eyebrows. FIG. 12 furthermore shows the cosmetic and/or medical treatments, which can be performed by a beautician, dermatologist, physician, specialist certified to do facial modifications, or plastic surgeon to realize these actions.

Figure 6:
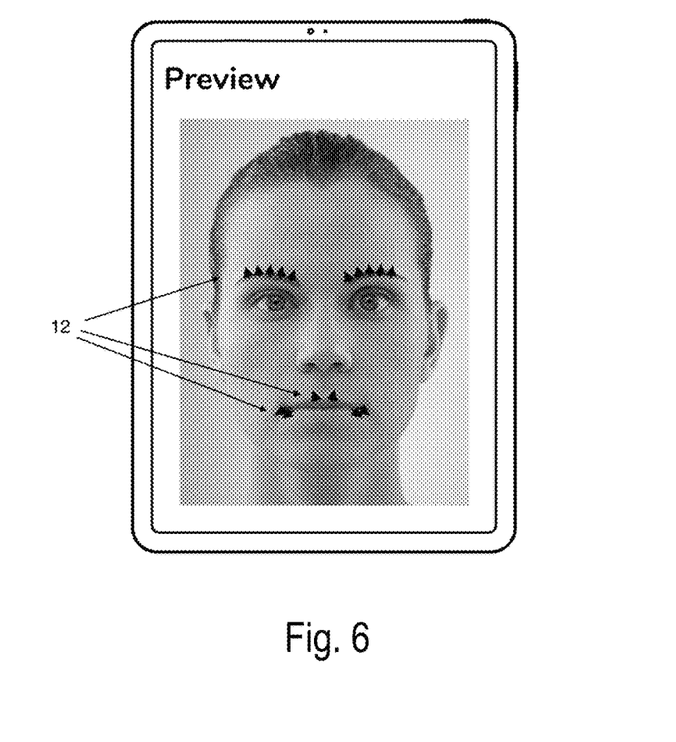
FIG. 6 shows the face of the person with a data set of modifications overlaid.

The result of a best match of modifications needed and modifications possible are then stored in the data set of modifications 12. This data set of modifications 12 technically describes what modifications are needed to modify visual data 4 of the face of person 2 to show the possible result of one or more invasive and/or minimally invasive cosmetic and/or medical treatments to improve the characteristic "competent" of person 2 in a computer-modified visual 13 of the face of a person 2 as shown in FIG. 6. FIG. 6 shows the face of person 2 with an overlay of arrows that indicate with regions of the face need to be treated to achieve the desired result of improved "competence". So for instance, the eyebrow position needs to be lifted and the volume of the jawline needs to be increased. The arrows shown are only symbolic as data set of modifications 12 may comprise further information about the face and processing of the visual data 4 needed.

In as seventh step of the method the visual data 4 of the face of the person 2 are modified based on the data set of modifications 12 and a computer-modified visual 13 of the face of the person 2 with the modification of the face achievable by the at least one proposed cosmetic and/or medical treatment is generated. If for instance artificial intelligence of the server 5 concluded that the eye bags of person 2 need to be tightened to improve the characteristic "attractiveness" of person 2, then the data set of modifications 12 may include information to soft focus the area of lower eyelid and zygoma in the visual data 4 of the face of person 2. Deep learning based application 7 or other conventional image processing methods like image warping therefore processes the photo or film of person 2 to provide the computer-modified visual 13 of the desired face of person 2. This seventh step may be processed by server 5 due to its large processing power, but could be processed by mobile device 3 as well. In this embodiment server 5 therefore comprises picture data modification means 14 to modify the visual data 4 of the face of person 2 according to the data set of modifications 12, which modified visual data 4 of the face of person 2 are transmitted to mobile device 3 and displayed as computer-modified visual 13 of the desired face of person 2 with mobile device 3.

In a preferred embodiment of the invention the artificial intelligence is used to automatically identify an area with wrinkles in the visual of the person's face based on technologies known to a man skilled in the art. Such areas for instance may be the area of lower eyelid and zygoma. The artificial intelligence may then be used to automatically soft focus these identified areas in case for instance the characteristic "attractiveness" of person 2 should be improved and the data set of modifications therefore includes such information to modify the visual of the face of the person to generate the computer-modified visual of the desired face of the person. In a further preferred embodiment, the artificial intelligence may also add wrinkles to the visual of a for instance young person's face, who wants to improve the characteristic "competence" in areas where elder people use to have wrinkles.

Figure 7:
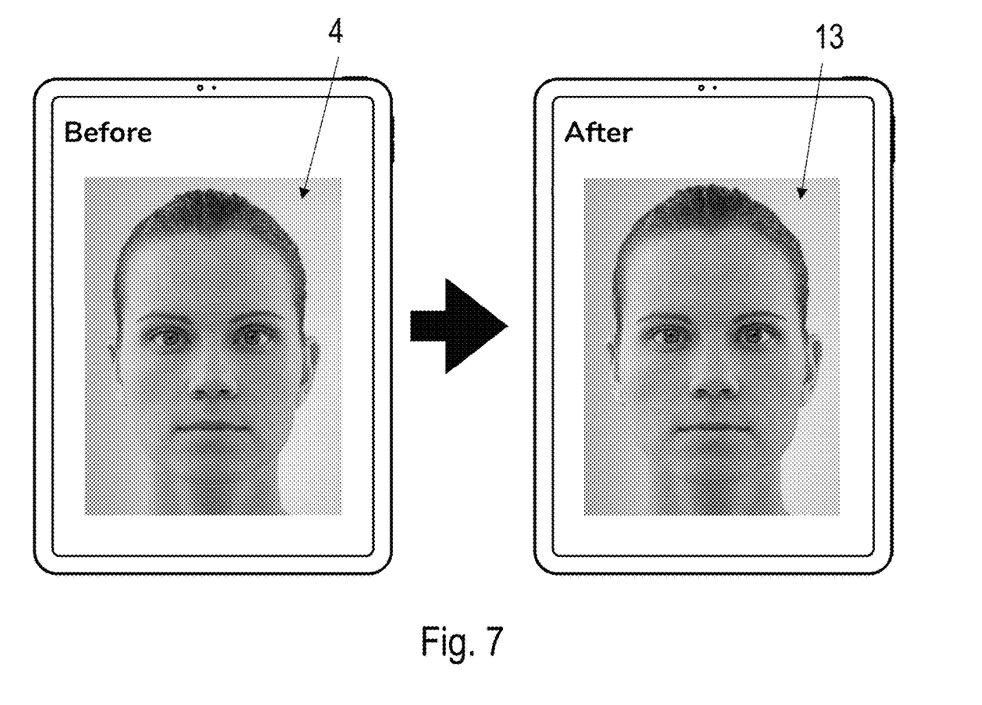
FIG. 7 shows a comparison of the original picture of the face of the person with the computer-modified visualization of the desired face of the person.
Figure 10:
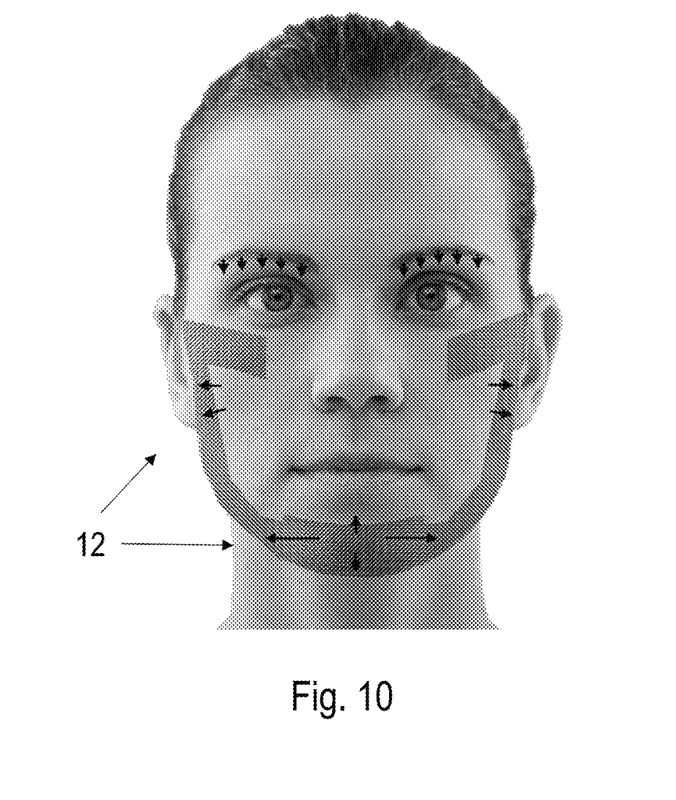
FIG. 10 shows a picture of a face with regions of the face marked to be treated to increase the characteristic "dominant" attributed to the person when making a first impression.

In an eighth step of the method the computer-modified visual 13 of the desired face of the person 2 is displayed with mobile device 3 as shown in FIG. 7. There are two preferred modes to display the visual data 4 of the face and the computer-modified visual 13 of the desired face of person 2 to enable him/her to easier see the differences. The first preferred mode is to use a toggle mode to alternatively show the taken standardized visual data 4 of the face of the person 2 and the computer-modified visual 13 of the desired face of the person 2. Person 2 just has to touch the display of mobile device 3 in a button area to toggle between the two visuals as fast as person 2 wants to see them to better see the differences and modifications. The second preferred mode is to use a marking mode to mark the areas of the face of the person 2 modified by the data set of modifications 12 as an overlay to the displayed computer-modified visual 13 of the desired face of the person 2 as shown in FIG. 10. Marking may be done e.g. with lines or broken lines overlaid over the computer-modified visual 13 of the desired face of the person 2. Both preferred modes enable person 2 to easily see those areas of the face that would need to be treated with invasive and/or minimally invasive cosmetic and/or medical treatments.

Figure 13:
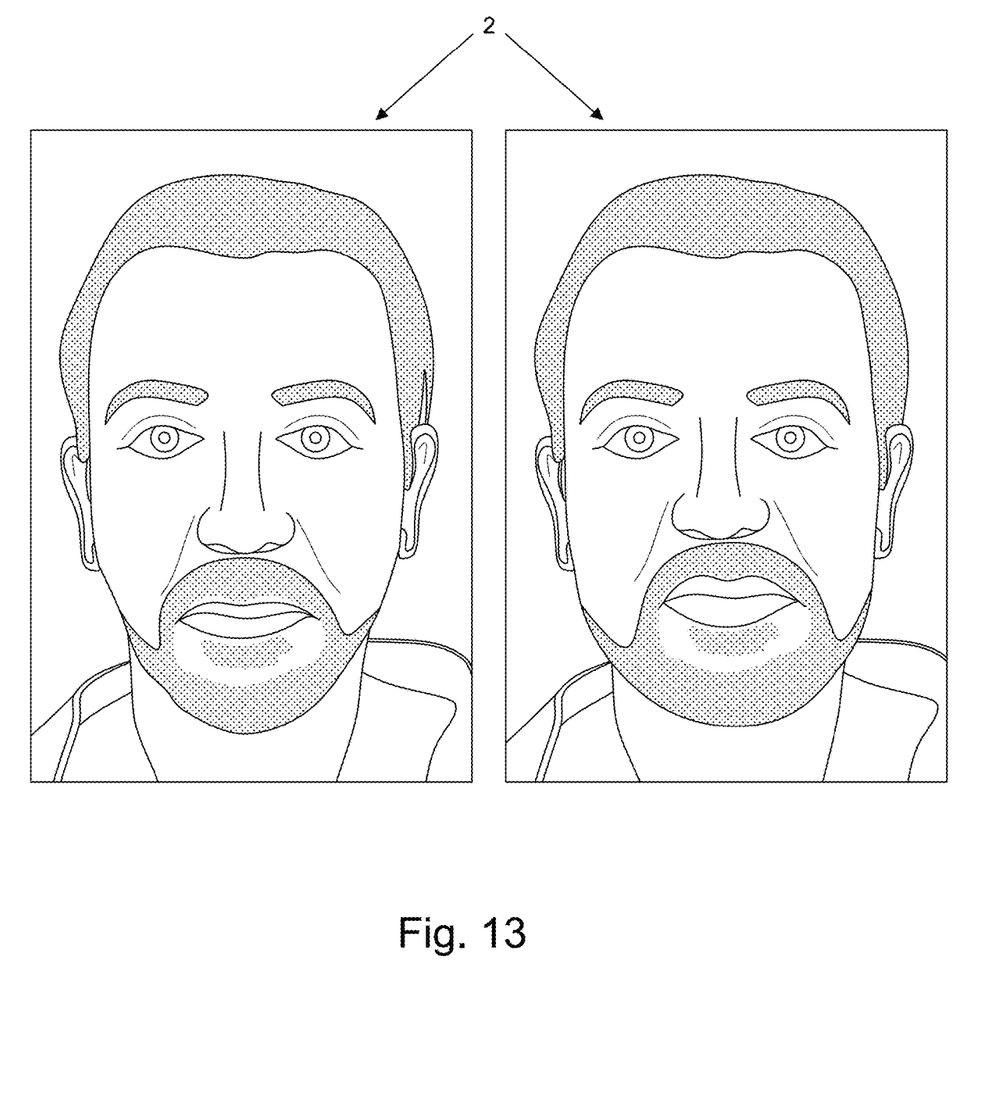
FIG. 13 shows a visual of a face of a person before and after the performance of the recommended treatments.

FIG. 13 shows the face of another person 2 before and after the recommended treatment was performed. The left photo shows person 2 who was interested to change the appearance of his face by increasing the characteristics "dominance" and "competence". The inventive method and system provided and displayed a computer-modified visual 13 of the desired face similar to the right photo and provided a recommendation to use the treatment of lipofilling in particular identified regions of the face. After the recommended treatment was performed, the right photo of FIG. 13 was taken and it turned out that the computer-modified visual 13 of the desired face was nearly identical to the actual photo taken after the treatment. This technical solution helps substantially to make informed decisions about cosmetic and/or medical treatments.

It is furthermore possible to display all invasive and/or minimally invasive cosmetic and/or medical treatments stored in database 9 and to select some of these invasive and/or minimally invasive cosmetic and/or medical treatments upfront to send these together with the visual data 4 of person 2 and the characteristic input by person 2 to change his/her facial appearance to server 5. In this case, the artificial intelligence of server 5 only uses those selected invasive and/or minimally invasive cosmetic and/or medical treatments during their search for a best match achievable for the data set of modifications 12 in the database 9 of visual modifications achievable by selected invasive and/or minimally invasive cosmetic and/or medical treatments. This enables person 2 to decide upfront which of the invasive and/or minimally invasive cosmetic and/or medical treatments are acceptable to be used to change his/her facial appearance and helps to streamline processing of server 5.

In case the sevenths step of above described method is processed by mobile device 3 and not on server 5, then mobile device 3 would comprise visual data modification means 14 to modify the visual data 4 of the face of the person 2 with the received data set of modifications 12 from server 5 by altering certain image vectors. The computer-modified visual 13 of the desired face of the person 2 is then displayed with the device 3. In another embodiment of the invention image processing by visual data modification means might be split between the server 5 and mobile device 3.

Deep learning based application 7 is optionally built to evaluate the age period, ethnicity and gender of person 2 in picture data 4. This helps to reduce data needed to be input when using the App.

Figure 8:
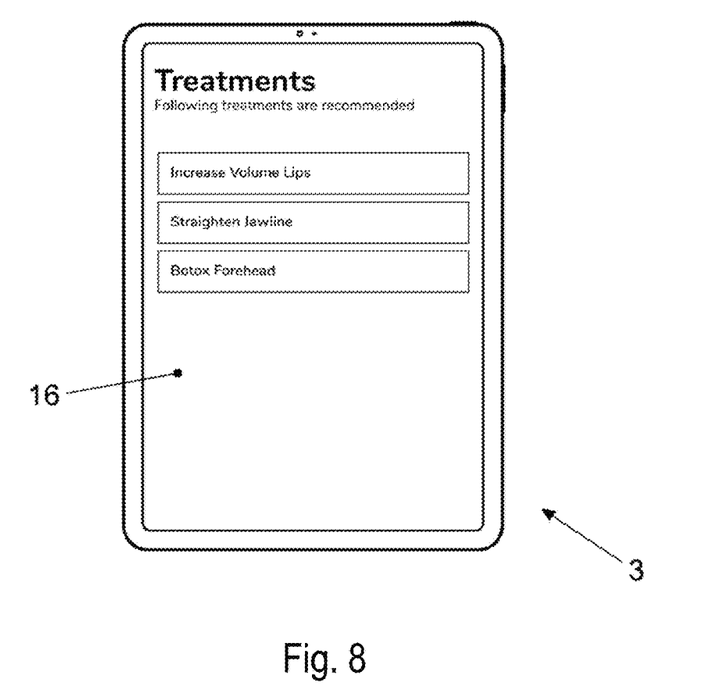
FIG. 8 shows a recommendation which treatments to use.
Figure 9:
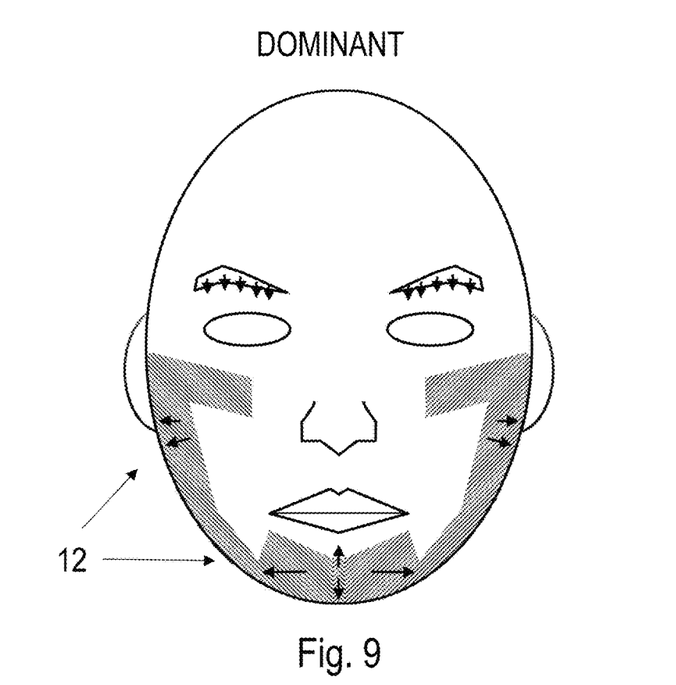
FIG. 9 shows a line drawing of a face with regions of the face marked to be treated to increase the characteristic "dominant" attributed to a person when making a first impression.

System 1 furthermore enables to show those invasive and/or minimally invasive cosmetic and/or medical treatments 16 on the display of mobile device 3 that have been selected by the artificial intelligence to achieve the desired face as shown in FIG. 8. Person 2 may decide to use a filter to select only some of the shown invasive and/or minimally invasive cosmetic and/or medical treatments, if for instance person 2 is not willing to undergo a surgical intervention. This selection of person 2 is sent to server 5, which calculates the necessary data set of modifications 12, which are achievable with the reduced number of invasive and/or minimally invasive cosmetic and/or medical treatments to achieve the desired changes in the characteristic (e.g. attractiveness).

It is furthermore possible to input more than one characteristic with input means of mobile device 3 as shown in FIG. 5. This provides the advantage that person 2 is free to improve two or more characteristics based on his/her personal interest.

It is furthermore possible that the person that uses the App is not the person that wants to change his/her appearance, but a person that wants to enable an informed decision like for example, a beautician, dermatologist, physician, specialist certified to do facial modifications or plastic surgeon.

In a further embodiment of the invention, the computer program realized as an APP of a mobile phone may be programmed to ask the user questions like the following: gender, age, profession, level of education, sexual orientation, religion and political orientation. These questions may be asked in the fifth step of above explained method about the user in one embodiment and about the target group, the user is interested in, in a second embodiment. This information may be used in the sixth step of above explained method, when generating the data set of modifications. The result of an analyse of the information about the user and/or the target group, the user is interested in, for which the user wants to be recognized as e.g. more "dominant" may be used as further input how characteristics of the user need to be modified. This has the advantage that the modifications closely fit the personal needs and wishes of the user.

In a further embodiment of the invention, an artificial intelligence system is used to provide an automated rating of the characteristic of the visuals of faces. Such artificial intelligence system may include a software to detect landmarks in the face of a person or any other conventional algorithm with the ability to do so.

The invention claimed is:
1. A method for providing a computer-modified visualization of a desired face of a person, comprising the steps of:
generating a first data set of visuals of faces and extracted face property data thereof linked to face characteristics data provided by a representative set of humans and storing the first data set, wherein the first data set is utilized to rate face characteristics of the visuals of faces;
extracting further face property data of the visuals of faces;
training an artificial intelligence to enable the artificial intelligence to provide an automated rating of the face characteristics of the visuals of faces using the extracted further face property data together with the generated first data set;
generating a second data set of visual modifications of a particular face achievable by a cosmetic and/or a medical treatment and storing the second data set;
taking a standardized visual of a particular face of a person;
inputting at least one desired characteristic of the particular face of the person to be changed;
using the artificial intelligence to analyse a particular visual of the particular face of the person and to generate a third data set of at least one desired visual modification of the person based on the at least one desired characteristic and at least one visual modification achievable by the cosmetic and/or the medical treatment;
modifying the standardized visual of the particular face of the person based on the third data set of the at least one desired visual modification;
generating the computer-modified visual of a desired face of the person with the at least one visual modification of the face achievable by the cosmetic and/or the medical treatment; and
displaying the computer-modified visual of the desired face of the person.

2. The method according to claim 1, further comprising the additional steps of:
using a toggle mode to alternatively show the standardized visual of the particular face of the person and the computer-modified visual of the desired face of the person, or
using a marking mode to mark areas of the displayed computer-modified visual of the desired face of the person modified by the third data set of the desired visual modifications as an overlay to the displayed computer-modified visual of the desired face of the person.

3. The method according to claim 1, further comprising the steps of:
displaying all of the cosmetic and/or the medical treatments stored in the second data set;
selecting only one or more of the cosmetic and/or the medical treatments displayed; and
using only the selected cosmetic and/or the medical treatments for the generation of the third data set.

4. The method according to claim 1, further comprising the additional steps of:
displaying the face characteristics; and
selecting two or more of the face characteristics displayed as the at least one desired characteristic to be used by the artificial intelligence to generate the third data set of visual modifications.

5. The method according to claim 1, further comprising the additional step of:
displaying a particular cosmetic and/or a particular medical treatment selected by the artificial intelligence to be used to generate the third data set of the at least one desired visual modification.

6. The method according to claim 1, further comprising the additional steps of:
using the artificial intelligence to analyse the particular visual of the particular face of the person to provide an automated rating of a particular face characteristic of the particular visual of the particular face of the person; and
displaying the particular face characteristics of the particular visual of the particular face of the person.

7. The method according to claim 1, further comprising the additional steps of:
using the artificial intelligence to automatically identify an area with wrinkles in the visual of the particular visual of the particular face of the person and to automatically soft focus the identified area.

8. A system for displaying a computer-modified visualization of a desired face of a person with a mobile device, wherein the mobile device comprises a display and a camera configured to input a face characteristic, and the mobile device is connected to a remote server which generates a data set of visual modifications, wherein:
the remote server comprises a deep learning based application to process the steps of the method according to claim 1 to generate a first database with data sets of visuals of faces and extracted face property data thereof linked to face characteristics and to generate a second database with the data set of visual modifications of a face achievable by cosmetic and/or medical treatments and the deep learning based application is built to generate the data set of visual modifications for at least one region of the face of the person to achieve a desired change in a particular face characteristic based on the generated databases; and
the remote server or the mobile device configured to modify visual data of the face of the person with the data set of visual modifications achievable by at least one cosmetic and/or medical treatment, wherein the modified visual data of the face are displayed with the mobile device.

9. A non-transitory computer readable medium storing a computer program comprising instructions which, when the program is executed by a computer, causes the computer to carry out the following steps to provide a computer-modified visualization of a desired face of a person:
generating a first data set of visuals of faces and extracted face property data thereof linked to face characteristics data provided by a representative set of humans and storing the first data set, wherein the first data set is utilized to rate face characteristics of the visuals of faces;
extracting further face property data of the visuals of faces;
training an artificial intelligence to enable the artificial intelligence to provide an automated rating of the face characteristics of the visuals of faces using the extracted further face property data together with the generated first data set;
generating a second data set of visual modifications of a particular face achievable by cosmetic and/or medical treatments and storing the second data set;
receiving a standardized visual of a particular face of a person from a mobile device;
receiving, from the mobile device, at least one desired characteristic of the particular face of the person to be changed;
using the artificial intelligence to analyse a particular visual of the particular face of the person and to generate a third data set of a desired visual modification of the person based on the inputted at least one desired characteristic and at least one of the visual modifications achievable by the cosmetic and/or the medical treatment;
modifying the standardized visual of the particular face of the person based on the third data set of the at least one desired visual modification;
generating the computer-modified visual of a desired face of the person with the at least one visual modification of the face achievable by the cosmetic and/or the medical treatment; and
transmitting the computer-modified visual of the desired face of the person to the mobile device to display the computer-modified visual.

10. The non-transitory computer readable medium according to claim 9, the computer program further comprising instructions which, when the program is executed by a computer, cause the computer to carry out the following additional steps of:
using a toggle mode to alternatively show the standardized visual of the particular face of the person and the computer-modified visual of the desired face of the person, or
using a marking mode to mark areas of the displayed computer-modified visual of the desired face of the person modified by the third data set of the desired visual modifications as an overlay to the displayed computer-modified visual of the desired face of the person.

11. The non-transitory computer readable medium according to claim 9, the computer program further comprising instructions which, when the program is executed by a computer, cause the computer to carry out the following additional steps of:
displaying all of the cosmetic and/or the medical treatments stored in the second data set;
selecting only one or more of the cosmetic and/or medical treatments displayed; and
using only the selected cosmetic and/or the medical treatments for the generation of the third data set of.

12. The non-transitory computer readable medium according to claim 9, the computer program further comprising instructions which, when the program is executed by a computer, cause the computer to carry out the following additional steps of:
displaying the face characteristics; and
selecting two or more of the face characteristics displayed as the at least one desired characteristic to be used by the artificial intelligence to generate the third data set of visual modifications.

13. The non-transitory computer readable medium according to claim 9, the computer program further comprising instructions which, when the program is executed by a computer, cause the computer to carry out the following additional steps of:
displaying all characteristics stored in the database; and
selecting two or more of the characteristics displayed as desired characteristic to be used by the artificial intelligence to generate the data set of modifications.

14. The non-transitory computer readable medium according to claim 9, the computer program further comprising instructions which, when the program is executed by a computer, cause the computer to carry out the following additional step of:
displaying a particular cosmetic and/or a particular medical treatment selected by the artificial intelligence to be used to generate the third data set of at least one desired visual modification.

15. The non-transitory computer readable medium according to claim 9, the computer program further comprising instructions which, when the program is executed by a computer, cause the computer to carry out the following additional steps of:
using the artificial intelligence to analyse the particular visual of the particular face of the person to provide an automated rating of a particular face characteristic of the particular visual of the particular face of the person; and
displaying the particular face characteristics of the particular visual of the particular face of the person.

16. The non-transitory computer readable medium according to claim 9, the computer program further comprising instructions which, when the program is executed by a computer, cause the computer to carry out the following additional steps of:
using the artificial intelligence to automatically identify an area with wrinkles in the visual of the particular visual of the particular face of the person and to automatically soft focus the identified area.

17. A system for providing a modified visual of a face of a person, comprising:
a remote server configured to:
generate a first data set of visuals of faces and extracted face property data thereof linked to face characteristics data provided by a representative set of humans and store the first data set, wherein the first data set is utilized to rate face characteristics of the visuals of faces;
extract further face property data of the visuals of faces;
train an artificial intelligence to enable the artificial intelligence to provide an automated rating of the face characteristics of the visuals of faces using the extracted further face property data together with the generated first data set;
generate a second data set of visual modifications of a particular face achievable by cosmetic and/or medical treatments and storing the second data set;
receive a standardized visual of a particular face of a person;
receive at least one desired characteristic of the particular face of the person to be changed;
use the artificial intelligence to analyse a particular visual of the particular face of the person and to generate a third data set of at least one desired visual modification of the person based on the at least one desired characteristic and at least one visual modification achievable by the cosmetic and/or the medical treatment;
modify the standardized visual of the particular face of the person based on the third data set of the at least one desired visual modification;
generate a computer-modified visual of a desired face of the person with the at least one visual modification of the face achievable by the cosmetic and/or the medical treatment; and
display the computer-modified visual of the desired face of the person.

18. The system according to claim 17, the remote server further configured to:
use a toggle mode to alternatively show the standardized visual of the particular face of the person and the computer-modified visual of the desired face of the person, or
use a marking mode to mark areas of the displayed computer-modified visual of the desired face of the person modified by the third data set of the desired visual modifications as an overlay to the displayed computer-modified visual of the desired face of the person.

19. The system according to claim 17, the remote server further configured to:
display all of the cosmetic and/or the medical treatments stored in the second data set;
select only one or more of the cosmetic and/or medical treatments displayed; and
use only the selected cosmetic and/or the medical treatments for the generation of the third data set of.

20. The system according to claim 17, the remote server further configured to:
display the face characteristics; and
select two or more of the face characteristics displayed as the at least one desired characteristic to be used by the artificial intelligence to generate the third data set of visual modifications.

21. The system according to claim 17, the remote server further configured to:
display all characteristics stored in the database; and
select two or more of the characteristics displayed as desired characteristic to be used by the artificial intelligence to generate the data set of modifications.

22. The system according to claim 17, the remote server further configured to:
display a particular cosmetic and/or a particular medical treatment selected by the artificial intelligence to be used to generate the third data set of at least one desired visual modification.

23. The system according to claim 17, the remote server further configured to:
use the artificial intelligence to analyse the particular visual of the particular face of the person to provide an automated rating of a particular face characteristic of the particular visual of the particular face of the person; and display the particular face characteristics of the particular visual of the particular face of the person.

24. The system according to claim 17, the remote server further configured to:
use the artificial intelligence to automatically identify an area with wrinkles in the visual of the particular visual of the particular face of the person and to automatically soft focus the identified area.

\* \* \* \* \*